United States Patent [19]

Weitz et al.

[11] 4,436,944

[45] Mar. 13, 1984

[54] PREPARATION OF O-XYLENE AND ETHYLBENZENE

[75] Inventors: Hans-Martin Weitz, Bad Durkheim; Rolf Fischer, Heidelberg; Hans H. Pohl, Deidesheim, all of Fed. Rep. of Germany

[73] Assignee: BASF Aktiengesellschaft, Fed. Rep. of Germany

[21] Appl. No.: 337,285

[22] Filed: Jan. 5, 1982

[30] Foreign Application Priority Data

Jan. 15, 1981 [DE] Fed. Rep. of Germany ....... 3101043

[51] Int. Cl.$^3$ .................................................. C07C 1/20
[52] U.S. Cl. .................................... 585/408; 585/418; 585/469; 585/407
[58] Field of Search ............... 585/408, 407, 418, 419, 585/420, 469; 252/466 R, 464

[56] References Cited

U.S. PATENT DOCUMENTS

| 2,172,540 | 9/1939 | Komarewsky | 585/420 X |
| 2,203,826 | 6/1940 | Komarewsky | 585/420 |
| 2,217,013 | 10/1940 | Grosse et al. | 585/418 |
| 3,480,684 | 11/1969 | Hansford | 585/420 |
| 3,758,600 | 9/1973 | Eberly et al. | 585/420 |

FOREIGN PATENT DOCUMENTS 538417 3/1957 Canada ................. 585/419
41-46173 of 1966 Japan .

OTHER PUBLICATIONS

G. F. Woods and A. Viola, J. Amer. Chem. Soc. 78 (1956), pp. 4380–4383.

Primary Examiner—Delbert E. Gantz
Assistant Examiner—A. Pal
Attorney, Agent, or Firm—Keil & Witherspoon

[57] ABSTRACT

O-xylene and ethylbenzene are prepared by converting, 2,7-octadien-1-ol, 1,7-octadien-3-ol or mixtures containing these octadienols, or carboxylates of 2,7-octadien-1-ol or of 1,7-octadien-3-ol, or mixtures containing these carboxylates at from 200° to 550° C. over a catalyst.

5 Claims, No Drawings

PREPARATION OF O-XYLENE AND ETHYLBENZENE

G. F. Woods and A. Viola, J. Amer. Chem. Soc. 78 (1956), 4380–4383, report that 2,4-octadien-6-ol is dehydrated at from 300° to 310° C. over aluminum oxide to give 1,6-dimethyl-1,3,5-hexatriene or 1-ethyl-1,3,5-hexatriene. If the reaction is carried out at from 450° to 500° C. instead of at from 300° to 310° C., substituted cyclohexadienes are obtained which are converted into mixtures of o-xylene and ethylbenzene only after dehydration over palladium/active charcoal.

It is an object of the present invention to provide a process for the preparation of o-xylene and ethylbenzene, the o-xylene and ethylbenzene being obtained in a one-stage reaction from the octadienols used.

We have found that this object and other advantages are achieved by a process for the preparation of o-xylene and ethylbenzene wherein 2,7-octadien-1-ol, 1,7-octadien-3-ol or mixtures containing these octadienols, or carboxylates of 2,7-octadien-1-ol or of 1,7-octadien-3-ol or mixtures containing these carboxylates, are converted at from 200° to 550° C. over a catalyst.

An advantage of the novel process is that o-xylene and ethylbenzene can be obtained in a one-stage reaction from the octadienols used, and particularly that the more valuable ethylbenzene is obtained as the principal product, together with only a small quantity of o-xylene. The preferential formation of ethylbenzene as opposed to o-xylene was surprising since it can be assumed that, in the reaction according to the invention, a dehydration or acid elimination first takes place to give octatriene, followed by a dehydrocyclization of the octatriene to give o-xylene and ethylbenzene. However, Japanese Patent Application 46,173 (1966) discloses that, in the dehydrocyclization of 1,3,6-octatriene, o-xylene is formed as the principal product, together with ethylbenzene.

The octadienols to be used as starting materials for the process of the invention are obtained, for example, by dimerization of butadiene, or of the butadiene contained in the $C_4$ cracking cut, in the presence of water, carbon dioxide and a palladium complex, for example according to the process of German Laid-Open Application DOS 2,018,054. 2,7-Octadien-1-ol or 1,7-octadien-3-ol, or mixtures of these octadienols, can be used as starting materials for the novel process. Correspondingly, the carboxylates of 2,7-octadien-1-ol or 1,7-octadien-3-ol can be used, individually or in the form of mixtures, as starting mateials, suitable examples of such carboxylates being those derived from aromatic carboxylic acids, for example benzoic acid, and preferably from lower aliphatic carboxylic acids, particularly from lower aliphatic monocarboxylic acids of, in general, 1 to 4 carbon atoms, preferably of 1 to 3 carbon atoms, such as formic acid, acetic acid and propionic acid.

The reaction according to the invention, ie. the dehydration and dehydrocyclization in one stage, is carried out in the presence of a catalyst, aluminum oxide or titanium dioxide, or a catalyst containing aluminum oxide or titanium dioxide, being preferred. When aluminum oxide is used as the catalyst, it can be advantageous for the catalyst to contain, in addition, oxides of elements of groups 5b, 6b and/or 8, and/or metals of group 8 of the periodic table according to Handbook of Chemistry and Physics, 49th edition, 1968–1969.

Examples of oxides which are suitable for addition to the aluminum oxide are vanadium oxide, eg. $V_2O_5$, vanadates, eg. alkali metal vanadates, chromium oxides, eg. $Cr_2O_3$, chromates, eg. alkali metal chromates, molybdenum oxide, eg. $MoO_3$, molybdates, eg. alkali metal molybdates, cobalt oxides, eg. $Co_2O_3$, and nickel oxides, eg. NiO. Examples of suitable metals of group 8 of the periodic table are palladium and, preferably, platinum. In general, the oxides are added to the aluminum oxide in quantities of from 0.1 to 50% by weight, preferably from 0.2 to 20% by weight, particularly from 0.5 to 10% by weight, based on aluminum oxide. If the aluminum oxide catalyst contains metals, the content of the latter is, in general, from 0.01 to 30% by weight, preferably from 0.02 to 20% by weight, particularly from 0.05 to 5% by weight, based on aluminum oxide.

The reaction according to the invention is carried out at from 200° to 550° C., preferably from 220° to 520° C., particularly from 230° to 500° C., and in general under atmospheric pressure or superatmospheric pressure, for example under 1.05–30 bar. However, the reaction can also be carried out under slightly reduced pressure.

It can be advantageous to react the octadienols, or their carboxylates, to be employed according to the invention, in a form diluted with hydrogen or with an inert gas, such as nitrogen, carbon dioxide or steam, or gaseous or vaporizable saturated and/or olefinically monounsaturated or polyunsaturated hydrocarbons, for example hydrocarbons of 1 to 8, preferably of 1 to 6, carbon atl, for example, for the preparation of phthalic anhydride.

The Examples which follow illustrate the invention.

EXAMPLES 1 TO 4 AND COMPARATIVE EXAMPLES 1 TO 3

The quantities, shown in grams in the Table, of octadienols or octatrienes are allowed to run dropwise, per hour, from a dropping funnel into a vaporizer heated to 200° C. The vaporized octadienol or octatriene is passed, in a nitrogen stream of 4 liters (S.T.P.) per hour, downwards through a reactor which consists of a vertical 30 cm long quartz tube having a diameter of 3.5 cm and containing 200 ml of catalyst. The reactor is brought to the reaction temperature by an external heater, the temperature being measured, at about 20 cm from the upper edge of the oven, by means of a thermocouple in the reactor packing. The reaction mixture is condensed in an ice-cooled collecting vessel and is subsequently analyzed by gas chromatography. The experimental conditions and experimental results are given in the table.

TABLE

| Example No. | Octadienol or octatriene employed (g) | Catalyst % by weight | Temperature °C. | Crude product g | Unreacted starting materials and intermediate products % by weight | Benzene % by weight | Toluene |
|---|---|---|---|---|---|---|---|
| 1 | 2,7-octadien-1-ol + 1,7-octadien-3-ol (molar ratio 7:1) | $Co_2O_3$ (5.0) $H_2MoO_4$ (13.5) $Al_2O_3$ | 400 | 40.5 | 5.9 | 0.9 | 2.7 |

TABLE-continued

| | | | | | | | |
|---|---|---|---|---|---|---|---|
| 2 | (63) 2,7-octadien-1-ol + 1,7-octadien-3-ol (molar ratio 5:1 in Example 2) (molar ratio 8:1 in Example 3) (57) | NiO (3.0) H$_2$MoO$_4$ (15) H$_3$PO$_4$ (6) Al$_2$O$_3$ | 400 | 34 | 8.1 | 0.8 | 2.1 |
| 3 | | | 300 | 27.8 | 30.3 | 0.2 | 0.4 |
| 4 | 2,7-octadien-1-ol (60) | Co$_2$O$_3$ (5.0) H$_2$MoO$_4$ (13.5) Al$_2$O$_3$ | 400 | 40 | 13.6 | 0.5 | 2.0 |
| Comparative Example 1 | 1,3,7-octatriene (54) | Al$_2$O$_3$ Co$_2$O$_3$ (5.0) | 300 | 45.3 | 7.0 | 1.2 | 5.9 |
| Comparative Example 2 | | H$_2$MoO$_4$ (13.5) Al$_2$O$_3$ | 400 | 34 | 7.2 | 0.3 | 0.9 |
| Comparative Example 3 | 2,4-octadien-6-ol (52) | NiO (3.0) H$_2$MoO$_4$ (15) H$_3$PO$_4$ (6) Al$_2$O$_3$ | 400 | 34 | 7.2 | 0.3 | 0.9 |

| Example No. | o-Xylene | m-Xylene | p-Xylene | Ethyl-benzene % by weight | Residual compounds | Ratio of ethyl-benzene:o-xylene |
|---|---|---|---|---|---|---|
| 1 | 26.3 | 4.2 | 1.2 | 39.8 | 19.0 | 1:0.66 |
| 2 | 23.6 | 4.3 | 1.2 | 39.1 | 20.8 | 1:0.60 |
| 3 | 9.0 | 0.7 | 0.4 | 29.1 | 29.9 | 1:0.31 |
| 4 | 21.1 | 1.8 | 0.5 | 35.5 | 25.0 | 1:0.60 |
| Comparative Example 1 | 28.9 | 4.4 | 1.6 | 23.8 | 27.8 | 1:1.21 |
| Comparative Example 2 | 39.1 | 1.5 | 0.6 | 31.1 | 9.7 | 1:1.26 |
| Comparative Example 3 | 45.7 | 2.2 | 0.4 | 27.8 | 15.5 | 1:1.64 |

We claim:

1. A process for the preparation of a mixture of o-xylene and ethylbenzene in a one-stage reaction, said mixture containing ethylbenzene as its principal product, which process comprises:
heating 2,7-octadien-1-ol, 1,7-octadien-3-ol or mixtures containing these octadienols, or carboxylates of 2,7-octadien-1-ol or of 1,7-octadien-3-ol, or mixtures containing these carboxylates at a temperature of from 200° to 550° C. over an aluminum oxide or titanium doxide catalyst to convert these starting materials to said mixture of o-xylene and ethylbenzene, ethylbenzene being the principal product of the mixture.

2. The process of claim 1, wherein aluminum oxide is used as the catalyst.

3. The process of claim 1, wherein titanium dioxide is used as the catalyst.

4. The process of claim 2, wherein the aluminum oxide contains oxides of elements of groups 5b, 6b and/or 8 of the periodic table.

5. The process of claim 4, wherein the aluminum oxide contains metals of group 8 of the periodic table.

* * * * *